United States Patent [19]

Bonnell et al.

[11] 4,203,444
[45] May 20, 1980

[54] SURGICAL INSTRUMENT SUITABLE FOR CLOSED SURGERY SUCH AS OF THE KNEE

[75] Inventors: Leonard J. Bonnell, Medford; Edward H. McHugh, Southboro; Douglas D. Sjostrom, Wakefield, all of Mass.; Lanny L. Johnson, Okemos, Mich.

[73] Assignee: Dyonics, Inc., Woburn, Mass.

[21] Appl. No.: 848,982

[22] Filed: Nov. 7, 1977

[51] Int. Cl.$^2$ .................. A61M 1/00; A61B 17/32
[52] U.S. Cl. .................. 128/276; 128/305; 128/752
[58] Field of Search ............ 128/305, 276, 2 B, 749, 128/750, 751, 752, 755; 30/340, 263

[56] References Cited

U.S. PATENT DOCUMENTS

| | | | |
|---|---|---|---|
| R. 27,032 | 1/1971 | Hall | 128/305 |
| 1,493,240 | 5/1924 | Bohn | 128/305 |
| 1,663,761 | 3/1928 | Johnson | 128/305 |
| 2,532,370 | 12/1950 | Perrill | 30/240 X |
| 3,618,611 | 11/1971 | Urban | 30/133 X |
| 3,732,858 | 5/1973 | Banko | 128/2 B |
| 3,734,099 | 5/1973 | Bender et al. | 128/305 |
| 3,844,272 | 10/1974 | Banko | 128/2 B |
| 3,882,872 | 5/1975 | Douvas et al. | 128/305 |
| 3,937,222 | 2/1976 | Banko | 128/305 |
| 3,945,375 | 3/1976 | Banko | 128/6 |
| 3,976,077 | 8/1976 | Kerfoot | 128/305 |
| 3,996,935 | 12/1976 | Banko | 128/276 |

*Primary Examiner*—Robert W. Michell
*Assistant Examiner*—Michael H. Thaler

[57] ABSTRACT

A surgical instrument useful in joint surgery for instance closed surgery of the knee. When in the form of a rotary vacuum shaver it comprises an external stationary tube having a side-facing, axially extending shaving port and an internal rotary blade capable of rotating at a slow speed, of the order of 200 rpm or below. Radial bearing portions at both proximal and distal ends radially support the blade in shearing relation to the external tube. A vacuum conduit draws fluid and articles to be shaved into the shaving port, and draws discrete shavings through the instrument, while the blade is driven at shearing speeds.

55 Claims, 16 Drawing Figures

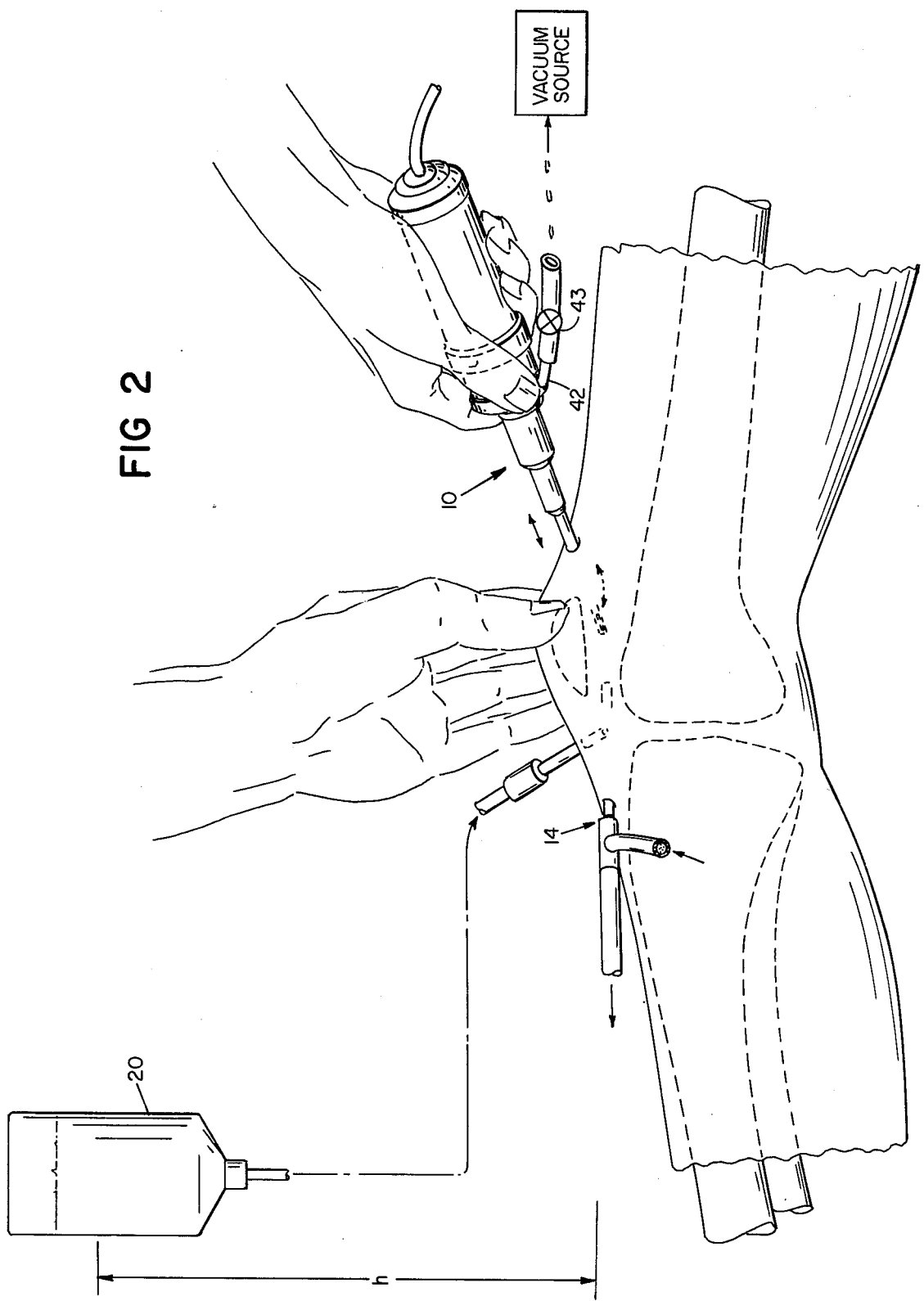

U.S. Patent May 20, 1980 Sheet 3 of 3 4,203,444
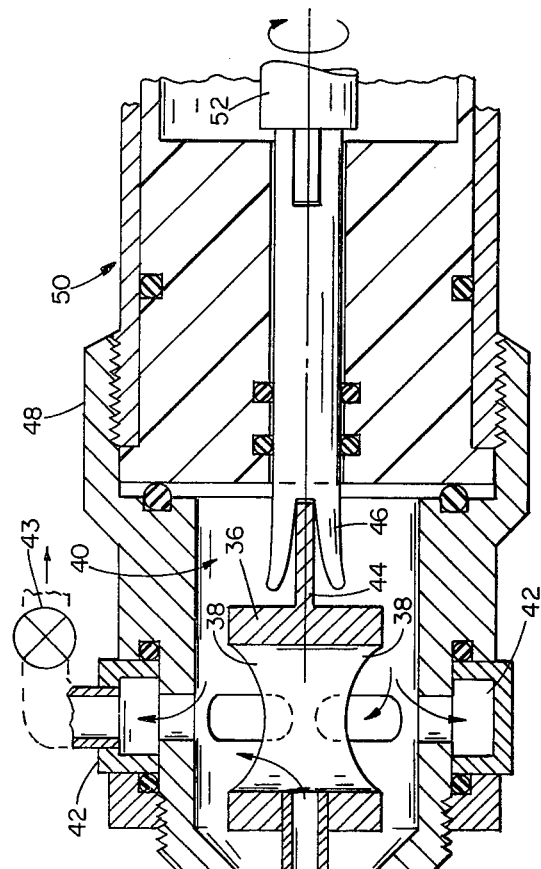
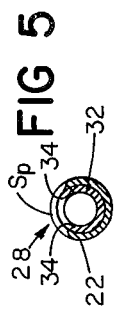
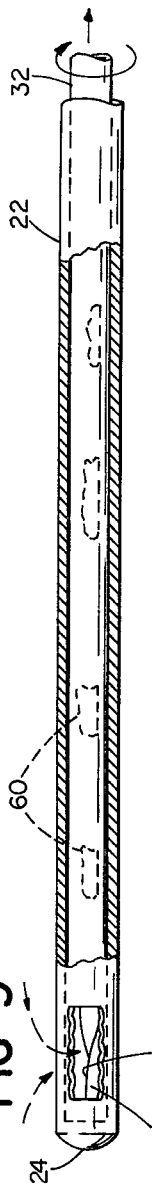
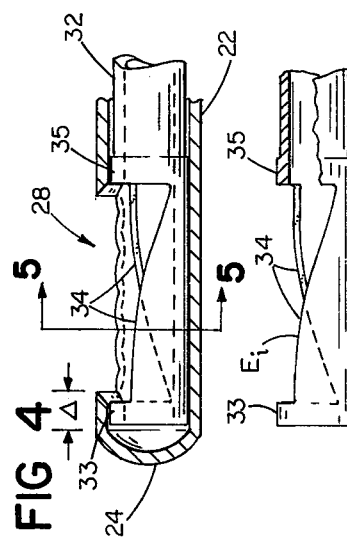
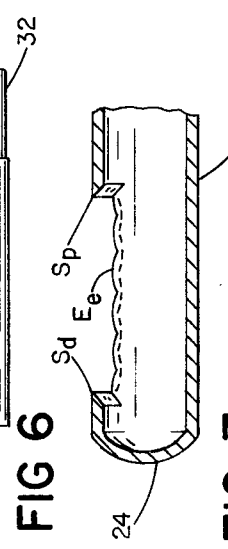
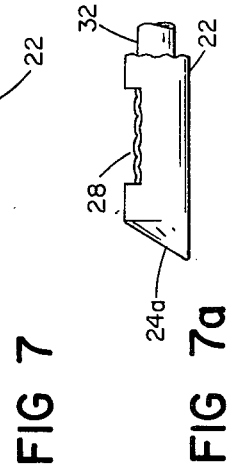
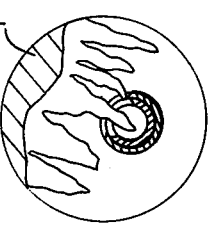
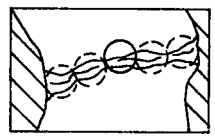
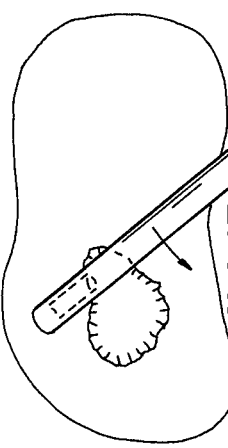
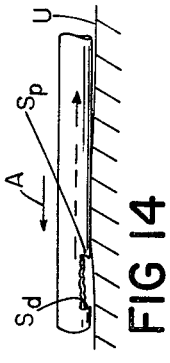

SURGICAL INSTRUMENT SUITABLE FOR CLOSED SURGERY SUCH AS OF THE KNEE

This invention relates to surgical instruments and in particular to instruments capable of performing intra-articular surgery by arthroscopy. The term "intra-articular" refers to joints of the body such as the knee and the term "arthroscopy" refers to viewing and surgical probes inserted through punctures into the joint region, without laying the joint open.

Although it was proven possible decades ago to visualize the joints of a human being by insertion of viewing probes, surgery of the joints has continued to be performed by open surgery. Thus, in a typical knee operation, although the object of the surgery for instance is to remove growths on the patella or to remove torn cartilage from the knee joint, a large incision is required. This takes a considerable time to heal which itself can cause trauma, discomfort, and limitations of movement.

To anyone who might contemplate closed surgery of the knee or other joint space, numerous restrictive and apparently conflicting requirements are encountered. For instance, the instrument should be small for maneuverability and ability to approach close to the bone but large in order to transmit the forces and to conduct away the matter to be removed; it should be safe from unwanted cutting but capable of definite strong cutting action when desired. And above all, it should be reliable and capable of use by surgeons of varying skill.

A principal object of this invention is to provide an instrument which is going beyond such conflicts successfully enables safe surgery to be performed using a probe inserted in a small puncture wound to reach the knee or other joint or region of the body.

According to the invention, it has been realized that a rotary surgical instrument suitable to the task is possible to provide by use of a vacuum shaving action in an instrument of special form. According to the invention, the instrument comprises a vacuum shaver having an external stationary tube defining a side-facing, axially extending shaving port and an internal member, closely fitting within the external tube, defining an internal, rotary blade which extends over the axial extent of the shaving port and preferably overlaps the port at both ends. This blade is preferably of helical inclination, adapted to coact with a close-lying cooperative axial edge of the external tube to produce a progressive shearing, shaving-like action. It is important that there be radial bearing portions at both proximal and distal ends of the internal blade, rotatably supported by corresponding portions of the external tube, to maintain the shearing relationship of the blades and that a vacuum conduit be provided for drawing objects to be shaved into the shaving port to draw the shavings through the instrument. A drive motor is adapted to rotate the blade at shearing speeds at which the material is cut into discrete shaved pieces, not masticated. It is found that the discreteness of the shaved pieces is important to the ability to transport the pieces through the instrument without jamming, and for the instrument to be self-purging.

The invention has particular importance to surgery of the knee. It is highly desirable for a practical instrument to be able to remove the relatively soft synovial material which is kelp-like and attached to the walls of the joint, the harder materials such as are found in patients with chondromalacia of the patella, and the difficult to cut gristle-like materials of meniscal cartilage that are found in the knee joint. It has been found that an instrument that is particularly successful in shaving all of these materials is provided by observing certain important relationships: The length of the side-facing port is about ¼ inch and this length and the internal diameter of the path through which the shavings must be removed bears a ratio in the range of 1.5 to 2.0 when the external diameter of the instrument is about 0.165 inch; the cutting blade is of helical form, with less than a full turn extending over the length of the shaving port; and the blade is rotated at speeds in the range between 100 and 200 rpm. It is found that by observing these limits, the various knee joint tissues to be removed are effectively drawn into the port and can be shaved into discrete shavings. These discrete shavings present frontal area that enables the force of the fluid to propel the shavings through the instrument, while the shavings remain sufficiently short to be drawn through the passage of the instrument (and thus out of the joint of the patient), without jamming the instrument. It is important that the radial bearings mentioned, effective at both ends of the cutting blade, cause the blade to be stiff against radial deflection, and therefore avoid jamming of the gristly meniscus material or other shavings between the moving and stationary members.

In preferred embodiments, both axial sides of the shaving port are formed as stationary cutting edges and the internal blade member, preferably in the form of a tube having a cut out, is adapted to cut while rotating in either direction, thus to enable the surgeon to move to either side within the knee joint, for removing undesired substances.

Furthermore, preferably both the distal and proximal ends of the shaving port are defined by scraping edges which are effective to remove material during axial movement of the instrument, with the scrapings free to move into the shaving port under the influence of the fluid flow. The invention also features an instrument dimensioned for optimum performance in interarticular surgery as a battery powered unit, the details of which will be given below in connection with the description of the preferred embodiment. This preferred embodiment will now be described with the drawings wherein:

FIG. 1 is a diagrammatic view showing the set-up of the instrument according to the invention with accessories for performing intra-articular surgery of the knee while FIG. 2 is a similar view showing the manner in which the surgeon's hands are used in manipulating the instrument relative to the patella;

FIG. 3 is a longitudinal cross-sectional view partially broken away view of the instrument of the preferred embodiment while FIG. 3(a) is a similar view of the tip of the instrument turned 90°;

FIG. 4 is a longitudinal cross-sectional view of the tip of the assembled instrument on an enlarged scale while FIG. 5 is a transverse cross section taken on lines 5—5 of FIG. 4;

FIG. 6 is a longitudinal view partially in cross section of the tip of the internal tube of the assembly while FIG. 7 is a similar cross-sectional view of the external tube of the assembly and FIG. 7(a) is a view of an embodiment having a snowplow-like tip for guiding certain materials to the shaving port;

FIG. 8 is a diagrammatic end view across section of the instrument showing its relation during the surgical procedure depicted in FIG. 1 to tissue of a patient affected by chondromalacia of the patella;

FIG. 9 is a longitudinal cross-sectional view of the instrument depicting the transport of shavings from the knee through the instrument;

Figure 1:
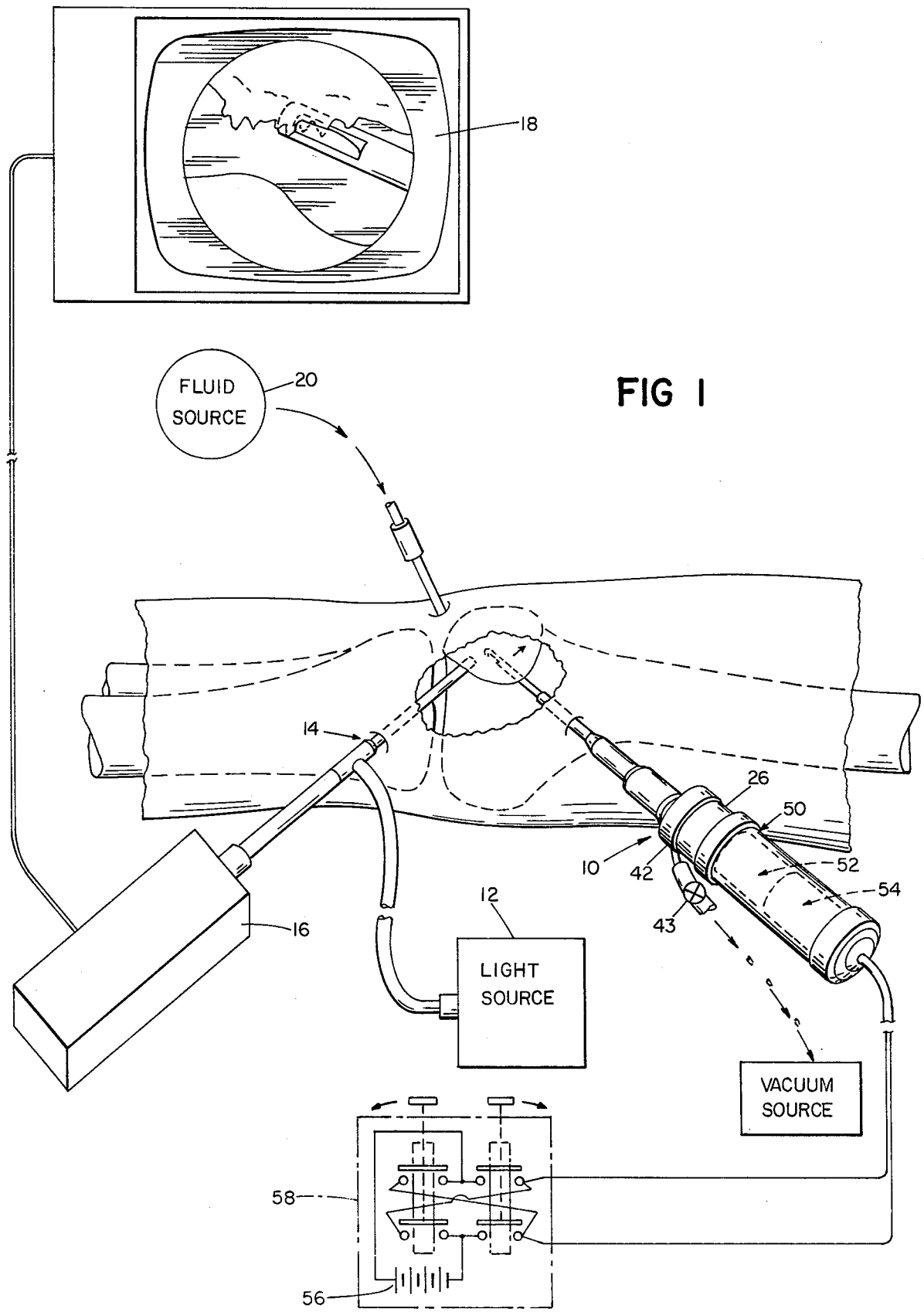

FIGS. 10, 11, and 12 are diagrammatic end views of the instrument showing respectively its relationship in shaving portions of the meniscus in a parrot beak tear and a bucket handle tear, and in shaving a lesion;

FIG. 13 illustrates the use of the instrument in smoothing an injured area of the tibial plateau; and FIG. 14 illustrates the axial movement and scraping action of the instrument.

Referring to FIGS. 1 and 2, the instrument 10 is shown inserted into the knee joint, below the patella. At the same time, a fiber optic device 14 introduces light to the interior of the joint from a light source 12 and returns a visual image along a separate bundle of fibers. While the image can be directed to an eyepiece for the surgeon, as well as to recording cameras, in the preferred embodiment shown the image is directed to television camera 16 which creates the display 18, which the surgeon watches in order to control his movements. By thus watching the screen, and manipulating the instrument and the patella as shown in FIG. 2, the instrument is caused to swing back and forth under the patella to shave the synovial tissue which is shown in the TV picture. A more detailed view of this is shown in FIG. 8 which will be described later herein.

During the operation, the knee joint is inflated by a hydrostatic leg of saline fluid created by elevated container 20.

The success of the instrument is dependent upon important aspects of its construction as has been noted previously. Referring to FIGS. 3 through 7, the instrument of the preferred embodiment comprises an external tube 22, here hypodermic tubing having an outer diameter of 0.165 inch and an internal diameter of 0.135 inch, this tube being approximately 5 inches long. At its distal end, the tube is closed by rounded end portion 24, formed of the tube material itself, e.g. by spinning, while its proximal end is rigidly joined to the end of housing 26. A sidefacing shaving port 28 is provided close to the distal end of the tube, having a length L=0.250 inch and a transverse chordal dimension d=0.125 inch. Within external tube 22 internal tube 32 is telescopically received in a close running fit at the shaving port and at both sides thereof with a clearance of e.g. less than 0.001 inch. Rings of material 33 and 35 of the internal tube 32 at distal and proximal ends of the blade thus serve as radial bearings for journaling the internal tube to the external tube. Downstream from journal 35 the external diameter of the internal tube is relieved, as by polishing, to reduce frictional drag. A ring 37, similar to rings 33, 35, however, is provided as bearing at the proximal end of the internal tube to journal it to the external tube. As shown in FIG. 6, for providing the blade, the region of the inner tube 32 which corresponds with the shaving port 28 in the external tube has a cut out, and the edges bounding this cut out define helical shearing edges 34 which are suitably sharpened. As will be seen in comparison with FIGS. 4, 6, and 7, these internal blades are slightly longer than the shaving port in order to assure that the blade overlaps beyond the edges of the shaving port. The longitudinal edges $E_e$ of the external tube, bounding the shaving port, are similarly sharpened to cooperate with the blade edges $E_i$ formed on the internal tube. The internal tube extends throughout the external tube and beyond the end wall of housing 26 to a transition element 36 which has a radially extending throughbore 38 connected to the internal bore of internal tube 32, for discharging fluid-borne particles. The housing 26 defines a hollow chamber 40 in which the transition element is disposed, and this chamber has a side outlet portion 42 connected to a vacuum source to which the material can readily flow, regardless of rotary position of the cutting tube. An axially extending spline element 44 extends beyond the transition member 36 and is adapted to axially interfit with drive element 46 which protrudes from the drive train 50. Thus, when the instrument is assembled, the internal tube housing 26, at its proximal end, has a threaded fitting 48 which is threaded to the exterior of the drive train 50. This drive train, as suggested in FIG. 1, includes reduction gears 52 and battery driven motor 54, the battery being located remotely and controlled by reversible switch 58.

Referring again to FIG. 3, it is seen that the longitudinal edges $E_e$ of the external tube at the shaving port are serrated, these serrations serving to prevent relative movement between the material and the instrument in the axial direction during the shaving action. On the other hand, the proximal and distal edges formed by the external tube 22 at the shaving port are undercut forming distal and proximal scraping edges $S_d$ and $S_p$ respectively.

It is important that the internal tube 32 have the radial bearing portions 33 and 35 at the distal and proximal ends of the cutting blades. These bearing portions provide stability of the cutting blade, in shearing relation to the stationary edges, by preventing radial deflection (it being found that even slight deflection, even on the order of one or two thousandths of an inch, of the rotating blade radially relative to the stationary blade can result in jamming of tissues cut from the knee). Also it is found that by providing the bearings as described, the frictional drag of the instrument is low, permitting the desired amount of torque to be achieved in a battery driven low-torque, safe instrument.

During the procedure as shown in FIGS. 1 and 2, the patient may be given only local anesthetic and perforations of the patient's flesh are made at selected points about the joint by a trocarring cannula. Liquid is introduced from source 20 into one cannula to inflate the joint pouch and the illumination and visualization instrument 14 is inserted through another cannula. Into a third cannula the instrument of FIG. 3 is inserted. The relationship of the cannula to the instrument is shown in FIG. 3 in dotted lines, the instrument being secured to the cannula by a leur lock upon insertion.

The flow through suction fitting 42 from the housing may be controlled by valve 43. The surgeon inserts the instrument with the motor deactivated. When the surgeon wishes to shave the material of the knee joint, he activates the valve 43 to cause the fluid flow, he guides the instrument to the tissue to be shaved, and steps on the foot pedal 58 to rotate the cutting blade in the desired direction. As shown in the television display 18 in FIG. 1, and in magnified view in FIG. 8, the instrument is used to shave away tissue formations of the under side of the patella of the knee joint, relative movement between the instrument and the patella being accomplished by movement of the patella by the surgeon's hand as well as by swinging the instrument back and forth and pushing it in and out as permitted. During all of these movements, the side-location of the shaving port enables ready viewing by the visual probe and the closed end of the instrument permits its use as a poker instrument without danger of damage. The fluid flow draws the material to be shaved into the shaving port and the blade rotating at the speed in the range of 100 to 200 rpm (frequency of shearing of the order about once to about three times per second) is effective, in each rotation, to produce a discrete shaving 60 which proceeds entrained in the fluid through the instrument in a "railroad train" sequence as depicted in FIG. 9. Due to the particular sizing of the shaving port relative to the interior diameter of the internal tube, and to the shaving speed, the discrete shavings are found to progress through the instrument without jamming. The material of the shavings, by staying intact, is in condition for ready analysis by the pathologist.

The surgeon proceeds with this instrument as suggested in the views of FIGS. 1 and 2. The inflating liquid renders the synovial tissue mobile so that it floats and can be displaced much as can be seaweed underwater. By moving the instrument, the synovial tissue is progressively shaved away, proceeding by repeated reciprocal motions in the axial direction and progressing from one side to the other. A point may be reached in which the remaining tissue cannot be effectively shaved with the internal shaving blade rotating in the direction shown in FIG. 5. The surgeon then activates the switch in the direction for opposite rotation and the opposite edge of the blade becomes effective on the opposite side of the shaving port, permitting the material to be reached. During this action the rounded end of the instrument serves as a probe and assures that anything being probed and pushed out of the way is not inadvertently cut.

Referring to FIG. 7(a), in this embodiment the distal end of the instrument is shaped in the form of a snowplow 24(a) and adapted, with axial movement in the direction of the arrow, to cause the material to be guided to the side of the instrument at which the shaving port 28 is located. Following the plow, the fluid flow is effective to guide the material into the shaving port for shaving action.

FIGS. 10 and 11 illustrate the instrument in its relationship to shaving away tears in rubber-like meniscal cartilege of the knee joint, the vacuum shaver being able to also act upon this material of difficult-to-cut consistency. The dotted lines in FIG. 11 illustrate the progressive positions that the instrument takes as the meniscus is gradually shaved away. FIG. 12 similarly shows the progressive action of the instrument in cutting away a lesion. FIG. 13 shows the vacuum shaver being drawn across the tibial plateau for smoothing an injured area. FIG. 14 shows the action of scraping blade $S_p$ as the instrument is pushed in the direction of arrow A, held against the under surface U of the patella. As the scraper blade $S_p$ removes material, the scrapings enter the influence of the moving fluid and are drawn into the shaving port and thus are expelled through the instrument from the surgical site.

In conclusion it is to be noted that a number of carefully conducted experimental procedures have been successfully performed with this instrument with the patient capable of walking immediately and with no feeling of pain or evidence of the surgery except for minor perforations about the knee joint.

The instrument itself is compact, durable, quiet to operate, and easily sterilized.

What is claimed is:

1. A surgical instrument for a joint space of the body characterized in that the instrument comprises an intra-articular shaver comprising an external stationary tube sized for insertion into said joint space, said external tube having a closed distal end and defining a side-facing, axially extending shaving port on the periphery only of said external tube and an internal member with close running fit with said external tube, defining an internal, rotary blade at said shaving port, said blade during each cycle constructed to open said port to the interior of the instrument and said blade having an axially extending edge adapted to co-act in shearing action with a cooperative axial edge defined by said external tube at said port to produce a succession of discrete shavings with progressive revolutions of said blade, said internal member having radial bearing portions at both proximal and distal ends of said blade, rotatably supported by corresponding portions of said external tube and effective to maintain said blade and edge in shearing relation, a vacuum conduit for drawing fluid and articles to be shaved into said shaving port and to draw said discrete shavings through the instrument, and a drive motor adapted to rotate said blade at a shearing speed of the order of 200 rpm or below that enables degenerated cartilage and synovial tissue of the joint to enter and be severed by said blade into discrete shavings for being transported away in succession through said vacuum conduit.

2. The intra-articular shaver of claim 1 capable of performing intra-articular closed surgery through a puncture wound, such as an operation on the knee, by arthroscopy, wherein said rotary blade is of generally helical form of sustantially less than one full turn over the length of said shaving port, said drive motor is adapted to rotate said blade at speed down to the order of 100 rpm, and said external tube is sized and constructed to enter the joint of the body through a puncture opening in the flesh of the body.

3. The intra-articular instrument of claim 2 wherein said internal member comprises an internal tube, a cut-out on the side wall of said internal tube positioned to match with said port in said external tube, an edge of said internal tube at said cut-out defining said blade.

4. The intra-articular instrument of claim 2 wherein distal and proximal of said cut-out, said internal tube provides full bearing rings for radially supporting said blade.

5. The intra-articular instrument of claim 2 wherein said external tube is about 0.165 inch external diameter and about 0.135 inch internal diameter, and wherein said port is approximately ¼ inch in axial length and has a chordal width of about ⅛ inch.

6. The intra-articular shaver of claim 2 wherein said external tube at both axial sides of said shaving port defines a respective pair of stationary cutting edges, said shaver blade having a respective pair of coacting edges adapted to cut with respective opposite directions of rotation, and said drive motor adapted selectively to drive said blade in opposite directions under the control of the surgeon.

7. The instrument of claim 6 wherein respective pairs of said edges of said port and coacting edges of said blade are arranged to provide progressive shearing in respectively opposite directions along the length of said external tube.

8. The intra-articular instrument of claim 2 including an enlarged chamber defined at the proximal end of said tubular assembly into which discrete cut particles and fluid progressively discharge from said tubular assembly.

9. The intra-articular instrument of claim 2 wherein said port extends axially about ¼ inch along said external tube.

10. The intra-articular instrument of claim 2 wherein the external diameter of said external tube is about 0.165 inch and wherein the ratio of the axial length L of said port to the internal diameter of the passage through which discrete particles are withdrawn is in the range of 1.5 to 2.0.

11. The instrument of claim 2 wherein said port is located immediately adjacent the distal end of said external tube and is elongated in the axial direction.

12. The intra-articular instrument of claim 1, wherein said internal member comprises an internal tube, a cutout on the side wall of said internal tube positioned to match with said port in said external tube, an edge of said internal tube at said cut-out defining said blade.

13. the intra-articular instrument of claim 12 wherein distal and proximal of said cut-out, said internal tube provides full bearing rings for radially supporting said blade.

14. The intra-articular instrument of claim 12 wherein said external tube is about 0.165 inch external diameter and about 0.135 inch internal diameter, and wherein said port is approximately ¼ inch in axial length and has a chordal width of about ⅛ inch.

15. The intra-articular shaver of claim 1 wherein at least one of the sides of said shaving port defined by said external tube comprises a scraping edge enabling scraping motion with said shaving port cooperating to receive resultant scrapings under the influence of said vacuum.

16. The intra-articular shaver of claim 1 having a distal end of the form of a plow, positioned to direct material to be cut sideways in the direction of said shaving port upon axial forward motion of said instrument.

17. The intra-articular shaver of claim 1 wherein said axial edge of said port is serrated, thereby serving, during coaction with said rotary blade, to resist axial movement of tissue along said port during said shearing action of said blade.

18. The intra-articular shaver of claim 1 wherein said external tube at both axial sides of said shaving port defines a respective pair of stationary cutting edges, said shaver blade having a respective pair of coacting edges adapted to cut with respective opposite directions of rotation, and said drive motor adapted selectively to drive said blade in opposite directions under the control of the surgeon.

19. The instrument of claim 18 wherein respective pairs of said edges of said port and coacting edges of said blade are arranged to provide progressive shearing in respectively opposite directions along the length of said external tube.

20. The intra-articular instrument of claim 1 including an enlarged chamber defined at the proximal end of said tubular assembly into which discrete cut particles and fluid progressively discharge from said tubular assembly.

21. The intra-articular instrument of claim 1 wherein said port extends axially about ¼ inch along said external tube.

22. The intra-articular instrument of claim 1, wherein the external diameter of said external tube is about 0.165 inch and wherein the ratio of the axial length L of said port to the internal diameter of the passage through which discrete particles are withdrawn is in the range of 1.5 to 2.0.

23. The instrument of claim 1, wherein said port is located immediately adjacent the distal end of said external tube and is elongated in the axial direction.

24. A surgical instrument for a joint space of the body characterized in that the instrument is an intra-articular shaver capable of performing closed surgery through a puncture wound, such as an operation on the knee, by arthroscopy, said instrument comprising an external stationary tube sized and constructed for insertion through a puncture in the flesh of the body into said joint space, said external tube having a closed distal end and defining a side-facing shaving port on the periphery only of said external tube and an internal member with close fit with said external tube defining an internal blade at said shaving port, said blade during each cycle constructed to open said port to the interior of the instrument and said blade having an edge set at an acute angle to and adapted to co-act in shearing action with a cooperative edge defined by said external tube at said port to produce a succession of discrete shavings with progressive passes of said blade, portions of said internal member adjacent to said blade supported by portions of said external tube to maintain said blade and edge in shearing relation, a vacuum conduit for drawing fluid and articles to be shaved into said shaving port and to draw said discrete shavings through the instrument, and a drive motor adapted to repeatedly move said blade at shearing speed past said edge of said port with a frequency of the order of about 3 times per second or below, that enables degenerated cartilage and synovial tissue of the joint to enter and be severed by said blade into discrete shavings for being transported away in succession through said vacuum conduit.

25. The instrument of claim 24, wherein said external tube at said port defines a respective pair of stationary cutting edges, said blade having a respective pair of coacting edges adapted to cut with respective opposite directions of movement, and said drive motor adapted to drive said blade in opposite directions.

26. The instrument of claim 25 wherein said drive motor is adapted selectively to drive said blade in opposite directions under the control of the surgeon.

27. The instrument of claim 25 wherein respective pairs of said edges of said port and coacting edges of said blade are arranged to provide progressive shearing in respectively opposite directions along the length of said external tube.

28. The instrument of claim 24, wherein the motor is adapted to move said blade past the edge of said shaving port with a frequency down to the order of one time per second.

29. The intra-articular instrument of claim 24 wherein said internal member comprises an internal tube, a cutout on the side wall of said internal tube positioned to match with said port in said external tube, an edge of said internal tube at said cut-out defining said blade.

30. The intra-articular instrument of claim 24 wherein distal and proximal of said cut-out, said internal tube provides full bearing rings for radially supporting said blade.

31. The intra-articular instrument of claim 24 wherein said external tube is about 0.165 inch external diameter and about 0.135 inch internal chamber, and wherein said port is approximately ¼ inch in axial length and has a chordal width of about ⅛ inch.

32. The intra-articular instrument of claim 24 including an enlarged chamber defined at the proximal end of said tubular assembly into which discrete cut particles and fluid progressively discharge from said tubular assembly.

33. The intra-articular instrument of claim 24 wherein said port extends axially about ¼ inch along said external tube.

34. The intra-articular instrument of claim 24 wherein the external diameter of said external tube is about 0.165 inch and wherein the ratio of the axial length L of said port to the internal diameter of the passage through which discrete particles are withdrawn is in the range of 1.5 to 2.0.

35. A surgical instrument for a joint space of the body,
the instrument capable of performing intra-articular closed surgery through a puncture wound, such as an operation on the knee, by arthroscopy, comprising an external stationary tube sized and constructed for insertion through a puncture in the flesh of the body into said joint space, said external tube defining a surgical port and an internal member with close fit with said external tube defining an internal blade at said port, said blade during each cycle constructed to open said port to the interior of the instrument and said blade having an edge set at an acute angle to and adapted to co-act in shearing action with a cooperative edge defined by said external tube at said port to produce a succession of discrete particles with progressive passes of said blade, portions of said internal member adjacent to said blade supported by portions of said external tube to maintain said blade and edge in shearing relation, a vacuum conduit for drawing fluid and articles to be sheared into said port and to draw said discrete particles through the instrument, and a drive motor adapted to repeatedly move said blade at shearing speed past said edge of said port with a frequency of the order of about 3 times per second or below, that enables degenerated cartilage and synovial tissue of the joint to enter and be severed by said blade into discrete particles for being transported away in succession through said vacuum conduit.

36. The intra-articular instrument of claim 35 wherein said internal member comprises an internal tube, a cut-out on the side wall of said internal tube positioned to match with said port in said external tube, an edge of said internal tube at said cut-out defining said blade.

37. The intra-articular instrument of claim 35 wherein distal and proximal of said cut-out, said internal tube provides full bearing rings for radially supporting said blade.

38. The intra-articular instrument of claim 35 wherein said external tube is about 0.165 inch external diameter and about 0.135 inch internal diameter, and wherein said port is approximately ¼ inch in axial length and has a chordal width of about ⅛ inch.

39. The intra-articular instrument of claim 35 including an enlarged chamber defined at the proximal end of said tubular assembly into which discrete cut particles and fluid progressively discharge from said tubular assembly.

40. The intra-articular instrument of claim 35 wherein said port extends axially about ¼ inch along said external tube.

41. The intra-articular instrument of claim 35 wherein the external diameter of said external tube is about 0.165 inch and wherein the ratio of the axial length L of said port to the internal diameter of the passage through which discrete particles are withdrawn is in the range of 1.5 to 2.0.

42. The instrument of claim 35 wherein said external tube at said port defines a respective pair of stationary cutting edges, said blade having a respective pair of coacting edges adapted to cut with respective opposite directions of movement, and said drive motor adapted to drive said blade in opposite directions.

43. The instrument of claim 42 wherein respective pairs of said edges of said port and coacting edges of said blade are arranged to provide progressive shearing in respectively opposite directions along the length of said external tube.

44. The instrument of claim 35 wherein the motor is adapted to move said blade past the edge of said shaving port with a frequency down to the order of one time per second.

45. A surgical instrument for a joint space of the body,
the instrument capable of performing intra-articular closed surgery through a puncture wound, such as an operation on the knee, by arthroscopy, comprising an external stationary tube sized and constructed for insertion through a puncture in the flesh of the body into said joint space, said external tube defining a surgical port and internal member with close running fit with said external tube defining an internal rotary blade at said port, said blade during each cycle constructed to open said port to the interior of the instrument and said blade having an axially extending edge set at an acute angle to and adapted to co-act in shearing action with a cooperative edge defined by said external tube at said port to produce a succession of discrete particles with progresive revolutions of said blade, said internal member having bearing portions at both proximal and distal ends of said blade, rotatably supported by corresponding portions of said external tube and effective to maintain said blade and edge in shearing relation, a vacuum conduit for drawing fluid and articles to be sheared into said port and to draw said discrete particles through the instrument, and a drive motor adapted to rotate said blade at a shearing speed of the order of 200 rpm or below that enables degenerated cartilage and synovial tissue of the joint to enter and be severed by said blade into discrete particles for being transported away in succession through said vacuum conduit.

46. The intra-articular instrument of claim 45 wherein said internal member comprises an internal tube, a cut-out on the side wall of said internal tube positioned to match with said port in said external tube, an edge of said internal tube at said cut-out defining said blade.

47. The intra-articular instrument of claim 45 wherein distal and proximal of said cut-out, said internal tube provides full bearing rings for radially supporting said blade.

48. The intra-articular instrument of claim 45 wherein said external tube is about 0.165 inch external diameter and about 0.135 inch internal diameter, and wherein said port is approximately ¼ inch in axial length and has a chordal width of about ⅛ inch.

49. The intra-articular instrument of claim 45 including an enlarged chamber defined at the proximal end of said tubular assembly into which discrete cut particles and fluid progressively discharge from said tubular assembly.

50. The intra-articular instrument of claim 45 wherein said port extends axially about ¼ inch along said external tube.

51. The intra-articular instrument of claim 45 wherein the external diameter of said external tube is about 0.165 inch and wherein the ratio of the axial length L of said port to the internal diameter of the passage through which discrete particles are withdrawn is in the range of 1.5 to 2.0.

52. The instrument of claim 45 wherein said external tube at said port defines a respective pair of stationary cutting edges, said blade having a respective pair of coacting edges adapted to cut with respective opposite directions of movement, and said drive motor adapted to drive said blade in opposite directions.

53. The instrument of claim 52 wherein respective pairs of said edges of said port and coacting edges of said blade are arranged to provide progressive shearing in respectively opposite directions along the length of said external tube.

54. The instrument of claim 45 wherein said port is located immediately adjacent the distal end of said external tube and is elongated in the axial direction.

55. The instrument of claim 45 wherein the motor is adapted to move said blade past the edge of said shaving port with a frequency down to the order of one time per second.

* * * * *

UNITED STATES PATENT AND TRADEMARK OFFICE
CERTIFICATE OF CORRECTION

PATENT NO. : 4,203,444

DATED : May 20, 1980

INVENTOR(S) : Leonard J. Bonnell, et al

It is certified that error appears in the above-identified patent and that said Letters Patent are hereby corrected as shown below:

Column 1, Line 32 "is" should be --in--.

Column 2, Line 40 "interarticular" should be --intra-articular--.

Column 2, line 65 "across" should be --cross--.

Column 5, Line 4 "of the order about" should be --of the order of about--.

Column 6, Line 31 "sustantially" should be --substantially--.

Column 8, Line 63 "chamber" should be --diameter--.

Signed and Sealed this

Twenty-eighth Day of October 1980

[SEAL]

Attest:

SIDNEY A. DIAMOND

Attesting Officer

Commissioner of Patents and Trademarks

REEXAMINATION CERTIFICATE (732nd)

United States Patent [19]
Bonnell et al.

[11] B1 4,203,444
[45] Certificate Issued Jul. 21, 1987

[54] SURGICAL INSTRUMENT SUITABLE FOR CLOSED SURGERY SUCH AS OF THE KNEE

[75] Inventors: Leonard J. Bonnell, Medford; Edward H. McHugh, Southboro; Douglas D. Sjostrom, Wakefield, all of Mass.; Lanny L. Johnson, Okemos, Mich.

[73] Assignee: Dyonics, Inc., Woburn, Mass.

Reexamination Request:
No. 90/000,650, Oct. 18, 1984

Reexamination Certificate for:
Patent No.: 4,203,444
Issued: May 20, 1980
Appl. No.: 848,982
Filed: Nov. 7, 1977

Certificate of Correction issued Oct. 28, 1980.

[51] Int. Cl.⁴ .................. A61M 1/00; A61B 17/32
[52] U.S. Cl. ........................... 604/22; 128/305; 128/752
[58] Field of Search ............................ 128/305

[56] References Cited

U.S. PATENT DOCUMENTS

| | | | |
|---|---|---|---|
| 2,369,925 | 2/1945 | Smith | 128/317 |
| 2,532,370 | 12/1950 | Perrill | 30/29 |
| 3,128,079 | 4/1964 | DeGriff | 253/3 |
| 3,214,869 | 11/1965 | Stryker | 51/273 |
| 3,618,611 | 11/1971 | Urban | 128/305 |
| 3,732,858 | 5/1973 | Banko | 128/2 B |
| 3,734,099 | 5/1973 | Bender et al. | 128/305 |
| 3,844,272 | 10/1974 | Banko | 128/2 B |
| 3,906,954 | 9/1975 | Boehr et al. | 128/305 |
| 4,014,342 | 3/1977 | Staub et al. | 128/305.1 |

FOREIGN PATENT DOCUMENTS

| | | |
|---|---|---|
| 2362157 | 12/1973 | Fed. Rep. of Germany |
| 2442516 | 9/1974 | Fed. Rep. of Germany |
| 719538 | 12/1954 | United Kingdom |
| 1286339 | 8/1972 | United Kingdom |
| 1349881 | 4/1974 | United Kingdom |

OTHER PUBLICATIONS

Article entitled "Electro-mechanical vitreous cutter and extractor" Transactions, Ophthalmology Society of the United Kingdom (1975), vol. 95, pp. 108–112.
Article entitled "Intraocular Microsurgery I. New Instrumentation (SITE)", Ophthalmic Surgery (1976), vol. 7(1), pp. 82–87.
Japanese U.M. Public Disclosure 28689/73 (with partial translation).
Product Literature, Surgical Design Corp.
Japanese Patent Public Disclosure 440099/77 (with a partial translation).
Felipe I. Tolentino et al., Arch. Opthalmol, vol. 93, Aug. 1975, pp. 667 to 672.

*Primary Examiner*—Michael H. Thaler

[57] ABSTRACT

A surgical instrument useful in joint surgery for instance closed surgery of the knee. When in the form of a rotary vacuum shaver it comprises an external stationary tube having a side-facing, axially extending shaving port and an internal rotary blade capable of rotating at a slow speed, of the order of 200 rpm or below. Radial bearing portions at both proximal and distal ends radially support the blade in shearing relation to the external tube. A vacuum conduit draws fluid and articles to be shaved into the shaving port, and draws discrete shavings through the instrument, while the blade is driven at shearing speeds.

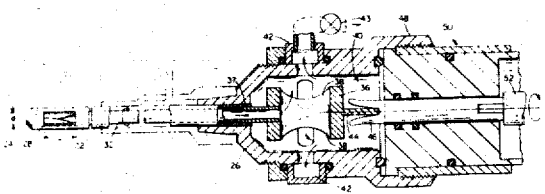

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 24–55 is confirmed.

Claims 1 and 2 are determined to be patentable as amended.

Claims 3–23, dependent on an amended claim, are determined to be patentable.

New claims 56–59 are added and determined to be patentable.

1. A surgical instrument for a joint space of the body capable of performing intra-articular closed surgery through a puncture wound, such as an operation of the knee, by arthroscopy, characterized in that the instrument comprises an intra-articular shaver comprising an external stationary tube sized *and constructed* for insertion into said joint space *through a puncture opening in the flesh of the body*, said external tube having a closed distal end and defining a side-facing, axially extending shaving port on the periphery only of said external tube and an internal member with close running fit with said external tube, defining an internal, rotary blade at said shaving port, said blade during each cycle constructed to open said port to the interior of the instrument and said blade having an axially extending edge adapted to co-act in shearing action with a cooperative axial edge defined by said external tube at said port to produce a succession of discrete shavings with progressive revolutions of said blade, said internal member having radial bearing portions at both proximal and distal ends of said blade, rotatably supported by corresponding portions of said external tube and effective to maintain said blade and edge in shearing relation, a vacuum conduit for drawing fluid and articles to be shaved into said shaving port and to draw said discrete shavings through the instrument, and a drive motor adapted to rotate said blade at a shearing speed of the order of 200 rpm or below *that enables degenerated cartilage and synovial tissue of the joint to enter and be severed by said blade into discrete shavings for being transported away in succession through said vacuum conduit*.

2. The intra-articular shaver of claim 1 [capable of performing intra-articular closed surgery through a puncture wound, such as an operation on the knee, by arthroscopy,] wherein said rotary blade is of general helical form of substantially less than one full turn over the length of said shaving port, said drive motor is adapted to rotate said blade at speed down to the order of 100 rpm[, and said external tube is sized and constructed to enter the joint of the body through a puncture opening in the flesh of the body].

56. *A method of surgery for a joint space of a human adult knee, comprising:*
   *introducing into the joint from outside the knee via puncture wounds in the flesh:*
      *a first conduit for introducing fluid from a fluid source,*
      *a visualization instrument, and*
      *an intra-articular surgical shaver instrument comprising:*
         *an external stationary tube sized for insertion into said joint space, said external tube having a closed distal end and defining a side-facing, axially extending shaving port on the periphery only of said external tube,*
         *an internal member with close running fit with said external tube defining an internal, rotary blade at said shaving port, said blade during each cycle constructed to open said port to the interior of the instrument, and said blade having an axially extending edge adapted to co-act in shearing action with a cooperative axial edge defined by said external tube at said port to produce a succession of discrete shavings with progressive revolutions of said blade, said internal member having radial bearing portions at both proximal and distal ends of said blade, rotatably supported by corresponding portions of said external tube and effective to maintain said blade and edge in shearing relation,*
         *a vacuum conduit for drawing fluid and articles to be shaved into said shaving port and to draw said discrete shavings through the instrument, and*
         *a drive motor adapted to rotate said blade at a shearing speed of the order of 200 rpm or below,*
   *introducing fluid through said first conduit into said joint and while actuating the means associated with said vacuum conduit for removing fluid to establish a substantial volume of flow of fluid through said joint sufficient to remove severed joint tissue and to provide a clear field for viewing through said visualization instrument,*
   *positioning the visualization instrument to enable observation of the area of the joint to be surgically treated,*
   *on the basis of said visual observation, positioning said surgical shaver instrument adjacent to said area of the joint and activating said surgical shaver instrument to enable degenerated cartilage and synovial tissue of the joint to enter and be severed by said blade into discrete shavings for being transported away in succession through said vacuum conduit.*

57. *A method of performing closed surgery of a joint space of a human adult knee, through a puncture wound, by arthroscopy, comprising:*
   *introducing into the joint from the outside the knee via puncture wounds in the flesh:*
      *a first conduit for introducing fluid from a fluid source,*
      *a visualization instrument, and*
      *an intra-articular surgical shaver instrument comprising:*
         *an external stationary tube sized and constructed for insertion through a puncture in the flesh of the knee into said joint space, said external tube having a closed distal end and defining a side-facing shaving port on the periphery only of said external tube,*
         *an internal member with close fit with said external tube defining an internal blade at said shaving port, said blade during each cycle constructed to open said port to the interior of the instrument* and said blade having an edge set at an acute angle to and adapted to co-act in shearing action with a cooperative edge defined by said external tube at said port to produce a succession of discrete shavings with progressive passes of said blade, portions of said internal member adjacent to said blade supported by portions of said external tube to maintain said blade and edge in shearing relation, a vacuum conduit for drawing fluid and articles to be shaved into said shaving port and for drawing said discrete shavings through the instrument, and a drive motor adapted to repeatedly move said blade at shearing speed past said edge of said port with a frequency of the order of about 3 times per second or below, introducing fluid through said first conduit into said joint while actuating said means associated with said vacuum conduit for removing fluid to establish a substantial volume of flow of fluid through said joint sufficient to remove severed joint tissue and to provide a clear field for viewing through said visualization instrument, positioning the visualization instrument to enable observation of the area of the joint surface to be surgically treated, on the basis of said visual observation, positioning said surgical shaver instrument adjacent to said area of the joint, and activating said surgical shaver instrument to enable degenerated cartilage and synovial tissue of the joint to enter and be severed by said blade into discrete shavings for being transported away in succession through said vacuum conduit.

58. A method of performing intra-articular closed surgery of a joint space of a human adult knee through a puncture wound by arthroscopy, comprising:

introducing into the joint from the outside the knee via puncture wounds in the flesh:

a first conduit for introducing fluid from a fluid source, a visualization instrument, and a surgical instrument comprising:

an external stationary tube sized and constructed for insertion through a puncture in the flesh of the knee into said joint space, said external tube defining a surgical port, an internal member with close fit with said external tube defining an internal blade at said port, said blade during each cycle constructed to open said port to the interior of the instrument and said blade having an edge set at an acute angle to and adapted to co-act in shearing action with a cooperative edge defined by said external tube at said port to produce a succession of discrete particles with progressive passes of said blade, portions of said internal member adjacent to said blade supported by portions of said external tube to maintain said blade and edge in shearing relation, a vacuum conduit for drawing fluid and articles to be sheared into said port and drawing said discrete particles through the instrument, and a drive motor adapted to repeatedly move said blade at shearing speed past said edge of said port with a frequency of the order of about 3 times per second or below, introducing fluid through said first conduit into said joint while actuating said means associated with said vacuum conduit for removing fluid to establish a substantial volume of flow of fluid through said joint sufficient to remove severed joint tissue and to provide a clear field for viewing through said visualization instrument, positioning the visualization instrument to enable observation of the area of the joint surface to be surgically treated, on the basis of said visual observation, positioning in said surgical instrument adjacent to said area of the joint and activating said surgical instrument to enable degenerated cartilage and synovial tissue of the joint to enter and be severed by said blade into discrete particles for being transported away in succession through said vacuum conduit.

59. A method of performing intra-articular closed surgery for a joint space of a human adult knee through a puncture wound by arthroscopy, comprising:

introducing into the joint from outside the knee via puncture wounds in the flesh:

a first conduit for introducing fluid from a fluid source, a visualization instrument, and a surgical instrument comprising:

an external stationary tube sized and constructed for insertion through a puncture in the flesh of the knee into said joint space, said external tube defining a surgical port, an internal member with close running fit with said external tube defining an internal rotary blade at said port, said blade during each cycle constructed to open said port to the interior of the instrument, and said blade having an axially extending edge set at an acute angle to and adapted to co-act in shearing action with a cooperative edge defined by said external tube at said port to produce a succession of discrete particles with progressive revolutions of said blade, said internal member having bearing portions at both proximal and distal ends of said blade, rotatably supported by corresponding portions of said external tube and effective to maintain said blade and edge in shearing relation, a vacuum conduit for drawing fluid and articles to be sheared into said port and drawing said discrete particles through the instrument, and a drive motor adapted to rotate said blade at a shearing speed of the order of 200 rpm or below, introducing fluid through said first conduit into said joint while actuating the means associated with said vacuum conduit for removing fluid to establish a substantial volume of flow of fluid through said joint sufficient to remove severed joint tissue and to provide a clear field for viewing through said visualization instrument, positioning the visualization instrument to enable observation of the area of the joint to be surgically treated, on the basis of said visual observation, positioning said surgical instrument adjacent to said area of the joint and activating said surgical instrument to enable degenerated cartilage and synovial tissue of the joint to enter and be severed by said blade into discrete particles for being transported away in succession through said vacuum conduit.

* * * * *